United States Patent [19]

Gregoire

[11] 4,134,291
[45] Jan. 16, 1979

[54] PROCESS FOR DETERMINING THE MOVEMENT RESISTANCE CHARACTERISTICS OF AN AUTOMOBILE VEHICLE

[76] Inventor: Jean A. Gregoire, 92, Avenue Niel, 75017 Paris, France

[21] Appl. No.: 887,140

[22] Filed: Mar. 16, 1978

[30] Foreign Application Priority Data

Mar. 29, 1977 [FR] France .................. 77 09392

[51] Int. Cl.² .......................................... G01M 17/06
[52] U.S. Cl. ........................................ 73/133 R; 73/9; 73/432 SD
[58] Field of Search ................ 73/9, 112, 116, 133 R, 73/117.3, 146, 432 SD

[56] References Cited

U.S. PATENT DOCUMENTS

| | | | |
|---|---|---|---|
| 3,921,446 | 11/1975 | Ludloff | 73/136 R |
| 3,955,410 | 5/1976 | Wakabayashi et al. | 73/133 R |
| 4,003,241 | 1/1977 | Thomas | 73/9 |
| 4,073,188 | 2/1978 | Slezinger et al. | 73/147 |

*Primary Examiner*—Charles A. Ruehl
*Attorney, Agent, or Firm*—Bucknam and Archer

[57] ABSTRACT

To determine the characteristics of resistance to movement of an automobile vehicle several test runs are made with the internal combustion engine and transmission replaced by a working electric motor and drive to the wheels, and dummy engine and drive components to simulate the airflow resistance of these parts. Two separate tests at the same speed are made with and without a tare weight and from the power absorbed by the electric motor, in each case measured in terms of the electric power fed to the motor, and taking into account the efficiency of the motor and of the drive transmission connecting it to the drive wheels, the delivered power is determined. Subtraction of the delivered power values gives an indication of the power loss due to the effect of the tare weight on the rolling resistance, and hence the rolling resistance coefficient. Knowing that either one of the delivered power values will be equivalent to the sum of rolling power losses and air drag power losses enables the just computed rolling coefficient to be used to compute the rolling power losses in either of the previous runs and thereby allows the air drag losses, and hence the aerodynamic drag coefficient to be calculated.

10 Claims, 2 Drawing Figures

PROCESS FOR DETERMINING THE MOVEMENT RESISTANCE CHARACTERISTICS OF AN AUTOMOBILE VEHICLE

The present invention refers to a process for determining the characteristics of an automobile vehicle.

The two principal factor components which combine to oppose to the forward movement of an automobile vehicle are: (a) the rolling resistance; and (b) the air resistance. Now, it is very important, for reducing the fuel consumption of a vehicle, (i.e. for cutting down energy losses), to know exactly the characteristics of the vehicle in this area.

The rolling resistance is that of the tires on the ground and, until quite recently, it had been verified that this rolling resistance was independent of the speed and that it was equal to:

$$R_r = k.W$$

k being the rolling coefficient and W the total weight of the vehicle. k was only approximately known and was estimated to be 10 to 15 kg per ton.

As a result of more recent work, it seems to have been conceded that the rolling coefficient k is not a constant but depends on the speed by a function of the nature of $$k = a + b V^2$$

In order to determine the rolling coefficient, the most commonly employed methods consist in turning a wheel inside or outside a large drum made of suitable material. By adding more or less weight to this wheel and measuring the changed rolling resistance, its rolling coefficient k can be measured.

In another method, a tricycle is used drawing a two-wheeled trailer to which more or less weight is added, the whole assembly being carefully streamlined to avoid air resistance on the trailer. A dynamometer measures the traction force on the two-wheeled trailer at constant speed of rolling and this is assumed to equal the rolling resistance force.

As can be verified, these methods are not very precise. They do not correspond exactly to the actual resistance of pneumatic tires on a real vehicle propelling itself along the road.

The exact value of the coefficient k is therefore not known, neither is the way in which it varies as a function of the speed, nor even how it varies as a function of the pressure of the pneumatic tires.

The air resistance is the sum of the profile resistance which the air opposes to its penetration by the profile of the vehicle and the drag resistance which is the drag force imposed on the vehicle by the passage of air under the bonnet. This last factor is not negligible, and can be as much as 30% of the total air resistance.

The air resistance increases as the square of the speed according to the formula:

$$R_a = C_x.S.V^2/16$$

$R_a$ = air resistance (i.e. aerodynamic drag force)
$S$ = frontal profile area
$V$ = speed
$C_x$ = aerodynamic coefficient of drag.

The most common present method of measurement is that of using a wind tunnel in which are placed models, preferably of 1/5 of normal size.

The data obtained contribute some useful indications but do not give the real value of $C_x$ for the vehicle on the road. It lacks the interaction of the road which is replaced by a polished metal plate and, if one tries to reproduce the passage of air under the bonnet, only a very rough simulation is obtained. One could equally put the full size vehicle in a large wind tunnel, but it would still lack the interaction of the road. In this case, there is not enough precision available in order to measure the effect of the fan under the bonnet.

In another process, the vehicle to be tested is pushed onto a track using another vehicle. A thrust strut equipped with a dynamometer allows the thrust force to be measured. This force represents the sum of the air resistance and the rolling resistance. In order to determine the air resistance, it is necessary only to subtract, from the observed total resistance, the rolling resistance measured with the conventional tricycle. It follows from this that the subtraction of two imprecise figures gives a doubly imprecise result.

As will be readily understood, all these processes give only approximate results. They are not precise enough, for example, to allow the influence of the pressure of the pneumatic tires on the rolling resistance to be measured.

In order to reduce to a minimum value the rolling resistance and the air resistance on existing vehicles under analysis, one must be able to measure them precisely.

In order to make modifications to these automobile vehicles in the direction of economy, the precision of these measurements is all the more essential since the results brought about by adjustments are slight. It is important to know whether these adjustments are going in the right direction and what are the exact percentages of economy that they bring.

Last of all, it is of enormous interest to be able to carry out all these measurements with the same precision on the prototypes of future models before tooling-up is begun.

The process according to the invention refers therefore to determining these resistance characteristics in an automobile vehicle.

According to the present invention a process is used in which an internal combustion engine is replaced by an electric traction motor fed by a source of current and the power absorbed by the electric motor is measured by means of a voltmeter and an ampmeter, taking into account the engine efficiency and the efficiency of the drive transmission from the motor to the drive wheel(s). Two successive comparative trials are carried out at the same speed, one P with the vehicle loaded with its normal load and the other with the vehicle overloaded with a tare t and, from the difference between the power P at normal load and the power $P_t$ when loaded with the tare, the rolling resistance $R_r$ and the rolling coefficient k are deduced. The air resistance $R_a$ is then calculated from the difference between the total resistance measured and the rolling resistance $R_r$, and from this the aerodynamic drag coefficient $C_x$ of the vehicle can be determined.

At the time of the trials, which will be described in detail hereafter, the power absorbed at the terminals of the electric traction motor is measured. Now, the figure which is of interest is the power actually used, that is to say the power at the wheel rim (tire tread). In order to obtain this figure, the power at the terminals of the electric motor, the efficiency of the motor and the efficiency of the drive transmission from the motor to the drive wheel(s) must be taken away.

It is therefore necessary beforehand to measure exactly these various efficiencies, and this can be easily done by known methods. The measurements on the vehicle to be tested are carried out on a track which is flat in both directions in order to eliminate wind effects. The trials should be carried out in a no more than slight wind, and with negligible cross-wind.

These measurements are carried out at a stabilized speed, by reading an ampmeter a voltmeter and a calibrated counter, by photographing these instruments, or by recording the amperages voltages speeds and times.

All these comparative trials are carried out at the same place and at the same height above the ground. The same conditions should be established at each trial, for example, with shock absorbers which will re-establish the chassis height despite a changed vehicle loading.

All these comparative trials are carried out at the same speed. Accordingly, the vehicle preferably carries a device allowing its speed to be regulated.

As far as the measurement of the rolling resistance is concerned, two comparative trials at the same speed are carried out successively, first of all with a vehicle having its normal load and then with a vehicle overloaded with a tare t of for example around 10% of its total weight. The respective powers P and $P_t$ are measured.

(i) Trial without tare:
p = rolling power loss ($P_r$) + air resistance power loss ($P_a$)

(ii) Trial with tare:
$P_t$ = tare rolling power ($P_{rt}$) + air resistance power loss ($P_a$).

As the speed, and therefore the air resistance, will be kept the same in both cases, subtraction of the two formulae gives:

$P_t - P = p_{rt} - p_r - (R_{rt} - R_r)V$ hence $P_t - P = Vk.t$

In this way one can calculate exactly the rolling coefficient k at the chosen speed.

The air resistance $R_a$ is obtained by substracting the rolling resistance $R_r$ (measured separately) from the measured total resistance force R where $R = P \div$ vehicle speed (V).

In this way one can calculate $C_x$, the actual aerodynamic coefficient of drag of the vehicle propelling itself along the road by the formula $$C_x = 16.R_a/S.V^2$$

The new process which has just been described allows the rolling resistance and the air resistance to be measured on a vehicle moving at a determined speed.

According to the invention, by measuring the rolling resistance at different speeds (for example, from 50 to 100 km/h) this process can equally allow the different values of the rolling coefficient k, as a function of the speed, to be determined. This also allows determination of the function by which k is related to the speed V. It is evident that if one wishes to determine precisely the different values of k, it is best to use a vehicle possessing a penetration coefficient in the air $S.C_x$ (S being the frontal profile area) which is as low as possible. In this way, the rolling resistance will be a high proportion of the total resistance and the measurements will be more precise.

Other projects and advantages of the invention will be better understood by perusal of the following description of one mode of execution, and by reference to the accompanying drawing in which.

Figure 1:
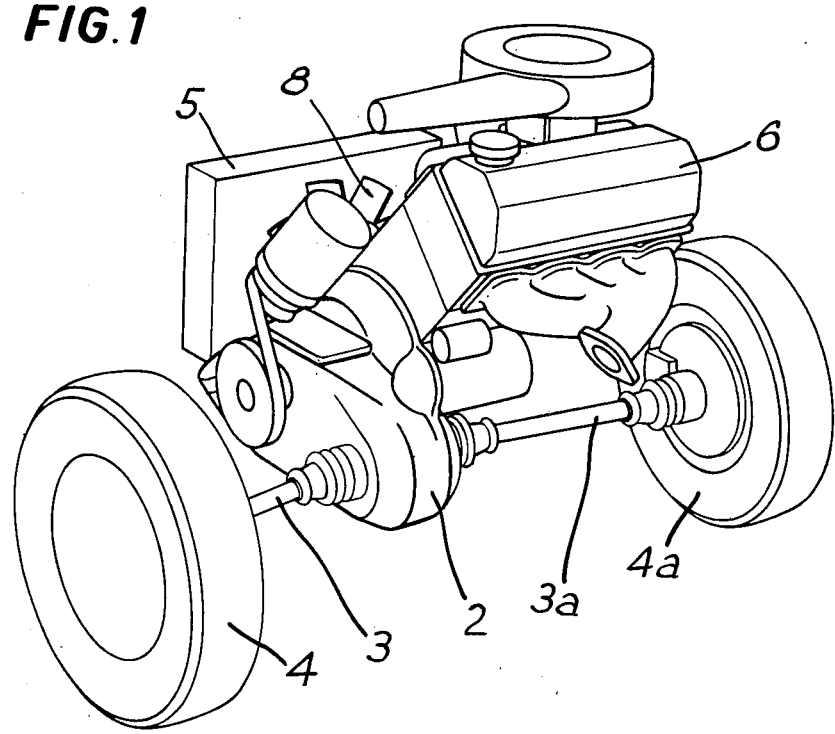
FIG. 1 is a perspective view of the traction unit, i.e. propulsion engine and transmission of a vehicle within its casing.

FIG. 1 shows the tractive components of a vehicle in which the internal combustion engine of an existing vehicle is connectecd to the drive input of a gear box 2 which transmits, via half-shafts 3, 3a, driving mmovement to the drive wheels 4, 4a.

Figure 2:
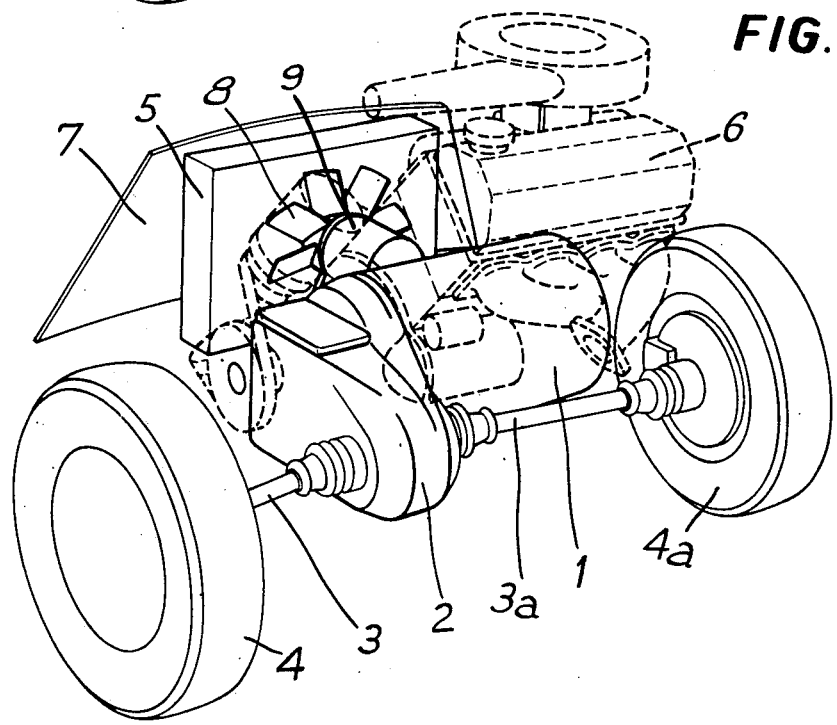
FIG. 2 is a similar perspective view, using the same direction of viewing as in FIG. 1, in which the internal combustion engine has been replaced by an electric motor and the mechanical parts (engine and accessories) are replaced by dummy models.

In FIG. 2, the internal combustion engine has been replaced by an electric motor 1. The diameter of this motor is smaller and its length less than that of the lower crank-case of the internal combustion engine, thus allowing it to be fitted easily into the location of the lower crank-case of the internal combustion engine.

Next, one provides a passage/vent for air under the bonnet exactly as it exists in the car. For this, one places in position the real radiator 5 as well as life-size models of all the parts which are found there, including the internal combustion engine and its accessories represented by dashed lines (FIG. 2). Outside the vehicle are placed all the usual parts (rear view mirror, exhaust pipe, etc.) or, failing this, life-size dummy models in their place.

The opening where the air enters under the bonnet is capable of being sealed by a detachable panel or cover 7 (FIG. 2). Close to the radiator 5, and preferably behind it, is a fan 8 which is driven by an auxiliary motor 9 at the same speed as would be the fan controlled by the normal internal combustion engine when the vehicle is travelling at a determined speed for the trial and with the selected gear ratio.

As with the principal traction motor 1, means are provided for allowing the power absorbed by the auxiliary motor 9 to be measured, taking into account the efficiency of said auxiliary motor.

The vehicle is equipped with electric batteries, not shown on the drawing, which are intended to supply power to the electric motors 1 and 9.

The test vehicle is stripped of all non-essential accessories, seats, fittings etc. to lighten it to the maximum so that when loaded with tare t its total weight does not reach the total weight of the original vehicle.

A means of electric control allows the vehicle to be maintained at a constant chosen speed.

In order to carry out the measurement of the rolling resistance, the entry of air under the bonnet (i.e. engine cooling air and vehicle heating/ventilating air) is blocked by the panel or cover 7 in such a way that the air resistance is minimal. Afterwards, the measurement of the rolling resistance is carried out in the manner described above, namely by carrying out two tests, one with tare t and the other without, and then subtracting.

As regards the measurement of air resistance, a first trial is made with the cover 7 in place, that is to say without air passing under the bonnet. The total power used up at the chosen speed is measured and, by subtracting the rolling resistance, the air resistance without passage of air under the bonnet is determined.

Next, the same measurements are carried out with air passing under the bonnet by removing the sealing cover or panel 7 but without driving the fan 8.

Thus, one obtains two air resistances, one without air passing under the bonnet, the other with air passing under the bonnet but without the fan assistance. These resistances allow two aerodynamic coefficients $C_x$ to be calculated, by the formula:

$$C_x = 16.R_a/S.V^2$$

Thus one obtains the two $C_x$ values for the vehicle; one with and one without air passing under the bonnet.

Thereafter, a third trial is carried out with air fan assisted air flow under the bonnet and the value of vehicle air resistance will now without doubt be lower than that without the fan assistance. At the same time the power consumed by this fan and its control is measured, allowing a precise assessment of the power used by the fan to be made.

As far as the measurement of the air resistance is concerned, it is preferable to carry out the trials with a wind not exceeding 3 m/second. It is also desirable to carry out such tests on a road in a straight line, protected from side winds and more particularly in a forest.

Although it is interesting to measure the resistances on existing automobile vehicles as well as the effect of modifications made, it is infinitely more useful to measure these characteristics on a new vehicle at the prototype stage. This allows the optimum body styling to be researched and allows the air flow pattern under the bonnet to be optimised before final tooling-up is begun.

In the above described trials, two cases may present themselves.

In a first case, the mechanical parts (engine and box housing) may be fixed onto a rigid chassis or sub-frame which can move on the road. It is then a question of electrifying it as is indicated above, before providing it with dummy bodywork as will be indicated later.

In a second case, these mechanical parts may be fixed onto a shell of thin sheet metal forming the bodywork. In order to make this mechanism mobile, it must be mounted on a test chassis or sub-frame which is sufficiently rigid to move, and presents exactly the same shape in its lower part as does the underside of the shell. As in the preceding case, this chassis or sub-frame will be electrified and provided with a model coachwork indicated hereafter.

All the front bodywork is executed, whether in sheet metal or in strengthened polyesters, with the fan and the air passages and vents under the bonnet identical to those of the future vehicle.

If the vehicle constructor does not have prototype bodywork in sheet metal available, the following procedure may be followed. Using, as a mold, a life-size model in plaster or modelling clay executed by the designers, he prepares bodywork, in reinforced polyesters, which is light in weight and simplified (e.g. by having a single door, a single seat and just the windscreen and the rear window in glass or in plexiglass). This bodywork, which thus presents the chosen shape, is fixed onto the chassis or the sub-frame. Its surface is painted or polished to have the finish of all-steel bodywork.

On this experimental vehicle, the test process described previously is carried out by electrifying it and placing in it either actually or dummy interior and exterior parts which will appear in the normal vehicle and the test vehicle is lightened as much as possible so that its weight is as close as possible to the weight of the real vehicle when empty.

It goes without saying that many modifications can be made, by the man skilled in the art, to the processes which have just been described solely by way of non-limiting examples, without departing from the framework of the invention as claimed hereinafter.

I claim:

1. A process for determining the movement resistance characteristics of an automobile vehicle on the road, comprising the steps of: (a) replacing the internal combustion engine of the vehicle by an electric traction motor fed by a source of current; (b) measuring the electrical power absorbed by the traction motor, and taking into account the engine efficiency and that of the transmission from the engine to the drive wheel(s) during two successive comparative trials at the same speed with the vehicle loaded with its normal load in one test and with the vehicle overloaded with a tare t on the other test to determine the useful power delivered at the drive wheels; (c) deducing the rolling resistance $R_r$ and the rolling coefficient k of the vehicle from the difference between the power P when loaded with normal load and the power $P_t$ when loaded with the load and tare; (d) calculating the air resistance $R_a$ from the difference between the total measured resistance and the rolling resistance $R_r$; and deducing from this the aerodynamic coefficient $C_x$ of the vehicle.

2. A process according to claim 1, wherein the vehicle under test is an existing production vehicle and the internal combustion engine is replaced by an electric motor having drive gearing at one of the reduction ratios of the gear box.

3. A process according to claim 1, wherein the vehicle under test is one which is not yet mass-produced and which has a chassis or sub-frame which is rigid enough for movement, and the electric motor is mounted on said chassis or sub-frame.

4. A process according to claim 3, wherein on the chassis or sub-frame, a full scale model, as light in weight as possible, is made reproducing the exact shape of the future bodywork in sheet metal.

5. A process according to claim 3, wherein on the chassis or sub-frame, a full scale model is made reproducing the exact shape of the future bodywork in reinforced polyesters which are as light as possible.

6. A process according to claim 1, wherein the vehicle under test is one which is not yet mass-produced, and is constructed in the form of a shell in thin sheet metal; and the process includes the step of building a chassis sufficiently rigid to carry the mechanical parts and for self-propelled movement of the vehicle, the lower part of the chassis having a shape identical to that of the shell and the electric motor is mounted upon said chassis.

7. A process according to any one of claims 1 to 6, and including the additional step of simulating the passage of cooling air under the bonnet, by placing into position on the vehicle the radiator and a life-size model of the internal combustion engine and of all its accessories made of at least one of wood, plastics or paper mâché.

8. A process according to claim 7, comprising providing a detachable cover, which once mounted on the vehicle blocks the entry of air under the bonnet, and carrying out separate tests at the same speed and vehicle loading, both with and without said cover to determine the air resistance with and without the passage of air under the bonnet, to enable calculation of the corresponding air drag coefficients $C_x$ to be determined.

9. A process according to claim 8, wherein the cooling air fan is driven by an auxiliary electric motor whose absorbed power is measured, and a comparison is thus made between the decrease in the traction power attributable to the air resistance of the fan and the actual power consumed by the fan on the separate tests made with and without the fan operating.

10. A process according to any one of claims 1 to 6, wherein the two trials are carried out travelling along a straight line on a track protected from cross winds.

* * * * *